US010167192B2

(12) United States Patent
In et al.

(10) Patent No.: US 10,167,192 B2
(45) Date of Patent: Jan. 1, 2019

(54) PERFORATED CONTACT ELECTRODE ON VERTICAL NANOWIRE ARRAY

(71) Applicant: The United States of America, as represented by the Secretary of the Navy, Washington, DC (US)

(72) Inventors: Hyun Jin In, Alexandria, VA (US); Christopher Field, Arlington, VA (US); Pehr E. Pehrsson, Fairfax Station, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 181 days.

(21) Appl. No.: 15/049,404

(22) Filed: Feb. 22, 2016

(65) Prior Publication Data

US 2016/0238554 A1 Aug. 18, 2016

Related U.S. Application Data

(63) Continuation of application No. 13/293,323, filed on Nov. 10, 2011, now Pat. No. 9,422,158.

(Continued)

(51) Int. Cl.
*G01N 27/12* (2006.01)
*B82Y 10/00* (2011.01)
(Continued)

(52) U.S. Cl.
CPC ............... *B82Y 10/00* (2013.01); *B82Y 15/00* (2013.01); *B82Y 30/00* (2013.01); *B82Y 40/00* (2013.01);
(Continued)

(58) Field of Classification Search
CPC .. B82Y 10/00; G01N 27/4146; G01N 27/127; H01L 29/456
(Continued)

(56) References Cited

U.S. PATENT DOCUMENTS

2005/0279638 A1* 12/2005 Babic ...................... C25D 1/08
205/78
2006/0138575 A1* 6/2006 Kamins ................. B82Y 15/00
257/419

(Continued)

OTHER PUBLICATIONS

Search Report in EP 11842108 (dated Jul. 25, 2017).
(Continued)

*Primary Examiner* — Farhana A Hoque
(74) *Attorney, Agent, or Firm* — US Naval Research Laboratory; Joseph T. Grunkemeyer

(57) ABSTRACT

Disclosed herein is a structure having: a support, a plurality of nanowires perpendicular to the support, and an electrode in contact with a first end of each nanowire. Each nanowire has a second end in contact with the support. The electrode contains a plurality of perforations. The electrode contains a plurality of perforations. Also disclosed herein is a method of: providing the above support and nanowires; depositing a layer of a filler material that covers a portion of each nanowire and leaves a first end of each nanowire exposed; depositing a plurality of nanoparticles onto the filler material; depositing an electrode material on the nanoparticles, the ends of the nanowires, and any exposed filler material; and removing the nanoparticles and filler material to form an electrode in contact with the first end of each nanowire; wherein the electrode contains a plurality of perforations.

14 Claims, 12 Drawing Sheets

Related U.S. Application Data

(60) Provisional application No. 61/413,664, filed on Nov. 15, 2010.

(51) Int. Cl.
  *B82Y 15/00* (2011.01)
  *B82Y 30/00* (2011.01)
  *B82Y 40/00* (2011.01)
  *H01L 29/06* (2006.01)
  *G01N 27/414* (2006.01)
  *H01L 29/45* (2006.01)
  *G01R 1/067* (2006.01)

(52) U.S. Cl.
  CPC ....... *G01N 27/127* (2013.01); *G01N 27/4146* (2013.01); *H01L 29/0665* (2013.01); *H01L 29/0676* (2013.01); *H01L 29/456* (2013.01); *G01R 1/06744* (2013.01); *H01L 2924/0002* (2013.01)

(58) Field of Classification Search
  USPC .................................................. 324/691, 663
  See application file for complete search history.

(56) References Cited

U.S. PATENT DOCUMENTS

| | | | |
|---|---|---|---|
| 2007/0023621 A1 | 2/2007 | Blick et al. | |
| 2008/0099339 A1* | 5/2008 | Zhou | B82Y 30/00 205/147 |
| 2009/0032801 A1* | 2/2009 | Parthangal | B82Y 10/00 257/14 |
| 2009/0267164 A1 | 10/2009 | Wunnicke et al. | |
| 2010/0024869 A1* | 2/2010 | Wang | H01L 31/028 136/249 |
| 2010/0176822 A1* | 7/2010 | Offermans | B82Y 15/00 324/663 |
| 2011/0189510 A1* | 8/2011 | Caracciolo | H01M 4/0421 429/50 |

OTHER PUBLICATIONS

Peng et al., "Motility of Metal Nanopartides in Silicon and Induced Anisotropic Silicon Etching" Ad. Func. Mat. 2008,18,3026-3035.
Office Action in JP 2015-142314 (dated May 19, 2017).
Peng et al., "Gas sensing properties of single crystalline porous silicon nanowires" Appl. Phys. Lett. 95, 243112 (2009).

\* cited by examiner

PERFORATED CONTACT ELECTRODE ON VERTICAL NANOWIRE ARRAY

This application is a continuation application of U.S. Pat. No. 9,422,158, issued on Aug. 23, 2016, which claims the benefit of Provisional Appl. No. 61/413,664, filed on Nov. 15, 2010. These applications and all other publications and patent documents referred to throughout this nonprovisional application are incorporated herein by reference.

TECHNICAL FIELD

The present disclosure is generally related to electrodes that may be used in sensors.

DESCRIPTION OF RELATED ART

Many types of nanowires, and other nanometer-scale structures of similar dimensions, have been at the heart of a large research effort aimed at studying their unique properties and integrating them into novel devices. For example, many different types of sensors have been fabricated from either single (Cui et al., *Science* 293 (2001) 1289) or an array of silicon nanowires (Engel et al., *Agnew. Chem. Int. Ed.* 49 (2010) 6830) to take advantage of the favorable physical, chemical, electrical, and optical properties of nanowires. For many device applications, such as gas sensors, a vertical nanowire orientation is ideal since it maximizes the surface area of nanowires that come in contact with the environment (Offermans et al., *Nano Lett.* 10 (2010) 2412), while also minimizing the deleterious effects of substrate oxides and other surface chemistry. These deleterious effects include trapping/detrapping of charge carriers, nonselective adsorption of other molecules on the substrate, and steric denial of part of the nanowire's surface to reaction with the target molecule. Furthermore, a large number of such nanowires in an array improves device performance by reducing 1/f noise and other noise types sensitive to the number of carriers.

A challenge in creating a sensor type device based on vertical nanowire arrays lies in making individual electrical connections to all the nanowires. The few existing approaches have involved embedding the entire nanowire array in some type of a sacrificial material, exposing the tips of the nanowires, and depositing the desired top contact electrode layer (Offermans et al., *Nano Lett.* 10 (2010) 2412; Park et al., *Nanotechnology* 19 (2008) 105503; Peng et al., *Appl. Phys. Lett.* 95 (2009) 243112). In these cases, the nanowire sensing region is exposed upon removal of the sacrificial material, and the substrate itself serves as the bottom electrode. Methods based on the deposition of a porous gold nanoparticle film on top of the nanowire array (Parthangal et al., *Nanotechnology* 17 (2006) 3786) and the random gap-bridging of nanowires during growth (Ahn, et al., *Appl. Phys. Lett.* 93 (2008) 263103) have also been investigated. In all these approaches, a non-ordered array of vertical nanowires was used as the main sensing element. More importantly, none of these methods are able to create a porous top contact electrode layer with holes of controllable size and distribution.

While various methods exist for creating porous electrodes (Lohmuller et al., *J. Micromech. Microeng.* 18 (2008) 115011; Kim et al., *Sens. Actuators, B* 141 (2009) 441-446), these methods are primarily designed for simply increasing the surface area of the electrode and are not applicable for creating such structures on top of a nanowire array. Other attempts, such as gold nanoparticle films (Parthangal et al., *Nanotechnology* 17 (2006) 3786) and electrospun metal nanofibers (Wu et al., *Nano Lett.* 10 (2010) 4242), do not allow precise control over the size and placement of holes in the electrode layer while also being significantly limited in the types of materials that can be used.

BRIEF SUMMARY

Disclosed herein is a structure comprising: a support, a plurality of nanowires perpendicular to the support, and an electrode in contact with a first end of each nanowire. Each nanowire has a second end in contact with the support. The electrode contains a plurality of perforations.

Also disclosed herein is a method comprising: providing a structure comprising: a support; and a plurality of nanowires perpendicular to the support, each nanowire having a second end in contact with the support; depositing a layer of a filler material that covers a portion of each nanowire and leaves a first end of each nanowire exposed; depositing a plurality of nanoparticles onto the filler material; depositing an electrode material on the nanoparticles, the ends of the nanowires, and any exposed filler material; and removing the nanoparticles and filler material to form an electrode in contact with the first end of each nanowire; wherein the electrode contains a plurality of perforations.

Also disclosed herein is a method comprising: providing a structure comprising a plurality of mutually parallel nanowires immobilized in a filler material; wherein the nanowires have exposed first ends on a first side of the structure; depositing a plurality of nanoparticles onto the filler material on the first side; depositing an electrode material on the nanoparticles, the first ends of the nanowires, and any exposed filler material on the first side; and removing the nanoparticles and filler material to form a first electrode in contact with the first end of each nanowire. The first electrode contains a plurality of perforations.

Also disclosed herein is a structure comprising: a support, a plurality of nanowires perpendicular to the support, and an electrode in contact with a first end of each nanowire. Each nanowire has a second end in contact with the support. The support is a second electrode or comprises an electrical contact on the surface opposed to the nanowires.

BRIEF DESCRIPTION OF THE DRAWINGS

A more complete appreciation of the invention will be readily obtained by reference to the following Description of the Example Embodiments and the accompanying drawings.

FIG. 1A: bar support; FIG. 1B: close-packed monolayer of nanospheres; FIG. 1C: nanospheres with reduced diameters; FIG. 1D: Au coating on the entire structure; FIG. 1E: Au etch template for Si etching; FIG. 1F: vertical SiNW array; FIG. 1G: vertical SiNW array with the Au removed; FIG. 1H: exposed tips of the SiNW array embedded in photoresist; FIG. 1I: second layer of nanospheres occupying gaps in the SiNW array; FIG. 1J: second layer of nanospheres with oxygen-plasma-reduced diameters; FIG. 1K: Au coating on the entire structure; and FIG. 1L: completed device showing the PTE and the SiNW array underneath.

FIG. 2A: close-packed monolayer of polystyrene nanospheres; FIG. 2B: nanospheres with oxygen-plasma-reduced diameters; FIG. 2C Au etch template for Si etching; FIG. 2D: vertical SiNW array; FIG. 2E: exposed tips of the SiNW array embedded in photoresist; FIG. 2F: second layer of nanospheres perfectly occupying gaps in the SiNW array; and FIG. 2G: completed device showing the PTE and the SiNW array underneath.

FIG. 4A: 1 ppm of $NH_3$, 500 ppb of $NH_3$, 1 ppm of $NO_2$, and 500 ppb of $NO_2$ at ~30% RH; and FIG. 4B: 250 ppb of $NO_2$, 50 ppb of $NO_2$ and 10 ppb of $NO_2$ at <10% RH.

DETAILED DESCRIPTION OF EXAMPLE EMBODIMENTS

Figure 1A:
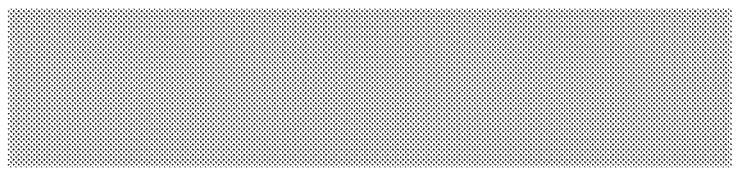
FIGS. 1A-L show schematic illustrations of cross-sectional and perspective views of the structure at various stages in the fabrication process.

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Microfabricated sensors based on nanostructures such as spheres, wires, rods, tubes, and ribbons have been the focus of intense research in an effort to achieve field deployable, gas or liquid phase sensors for detection of chemical warfare agents and explosives. Such sensors would be selective and sensitive, miniature, low power, fast, economical, simple-to-use, and capable of detecting a wide range of analytes in complex environments such as a battlefield or an airport. The unique electrical and mechanical properties of nanostructures give them great potential but also problems in gas phase sensing platforms such as chemical field-effect transistors (ChemFETs). For example, prototype nanoscale devices are more sensitive to analyte adsorption than macroscale bulk devices because of their high surface-to-volume ratios. However they also have relatively poor signal-to-noise ratios due to shot noise and 1/f noise, which are more significant at the nanoscale. Single nanowires can respond quickly to the analyte; however, diffusion-limited mass transport through a nanowire array prevents simultaneous response by all of the nanowires and hence increases response time. A good nanostructure-based gas sensor maximizes the surface area of the sensing element, reduces or eliminates charge carrier related noise sources, and minimizes diffusion-hindered response time.

Silicon nanowires may meet the requirements of such an ideal nanostructure-based sensor. They are easy to fabricate with existing silicon fabrication techniques that reduce cost and ensure integrability with conventional CMOS devices. Vertical arrays offer significant advantages by minimizing major noise sources at the nanoscale and maximizing sensor surface area; noisy wire-to-wire junctions are eliminated and the wire surface is not blocked by the supporting substrate. Additionally, vapor diffusion through vertically aligned silicon nanowire arrays is critical because hindered diffusion increases the response time.

Disclosed herein is a method for creating arrays of vertical nanowires, especially ordered arrays, either with a solid top electrode or a top electrode with an array of holes, especially a periodic and well-defined array of holes. The holes in the top contact electrode layer may allow various elements, such as gases or liquids, to flow rapidly through it and come in contact with the sensing nanowire region underneath. The holes or perforations may be sized and located such that electrical contact will be established to the tips of the nanowires in the array while maximizing the overall porosity of the electrode layer. In the case of the ordered arrays, the periodic placement may maximize the influx of gas or liquid from the side of the wires comprising the array. In some configurations, there may be clear channels all the way through the array. Likewise, the nanowires in an ordered array usually have similar or identical dimensions and pitch, thus minimizing wire to wire variations and allowing selection of the dimensions giving the best response. Disordered nanowire arrays may still benefit from the porous top electrode, which provides another avenue for rapid target molecule ingress to all of the nanowires comprising the array.

The support and nanowires can be any material that is compatible with the electrical measurement to be performed, including but not limited to semiconducting, conducting, metallic, or insulating material. There may be an electrical connection between the nanowires and the support. One example support material is silicon, such as a silicon wafer. The support may be a substrate or another electrode, including the perforated electrode described herein. The support may include an electrical contact on the surface opposed to the nanowires.

The nanowires may be made of the same material as the support or of a different material, and may be, for example, silicon, single-wall carbon nanotubes, multi-wall carbon nanotubes, or gallium nitride. The properties of the nanowire material may be either controlled or not. In the case of controlled material, this includes, for example, composition, doping and electrical conductivity, crystallinity, chemical functionalization, and additional surface layers.

There are a plurality of nanowires that are perpendicular to the support having only the second end in contact with the support. However, additional nanowires that are not perpendicular to the support may also be present. As used herein, "perpendicular" may be defined as within 1°, 5°, 10°, 20°, 40°, or 60° of normal to the support. The nanowire dimensions may be either uncontrolled or controlled as to, for example, length, diameter, and crystal face. They may be of uniform length in that they are all of a length that is within 1%, 5%, 10%, or 20% of their average length.

Methods of forming nanowires on a support are known in the art, including but not limited to methods disclosed in Huang et al., *Adv. Mater.* 23 (2011) 285-308; Kayes et al., *Appl. Phys. Lett.*, 91 (2007) 103110; Lee et al., *Nano Lett.* 10 (2010) 1016-1021; Weisse et al., *Nano Lett.* 11 (2011) 1300-1305; and Offermans et al., *Nano Lett.* 10 (2010) 2412-2415. The nanowires and support may both be made from the same precursor substrate. This may be done by etching the precursor substrate to leave behind the nanowires and the support. Other methods include, but are not limited to, growing the nanowires on the support and attaching pre-formed nanowires to the support. Growth methods include, but are not limited to, chemical vapor deposition (catalyzed or uncatalyzed), physical vapor deposition, molecular beam epitaxy and related growth methods, and growth in a liquid.

In some embodiments, an ordered array of vertical nanowires can be etched into (Peng et al., *Adv. Mater.* 14 (2002) 1164) or grown out of (Westwater et al., *J. Vac. Sci. Technol. B* 15 (1997) 554) a substrate of various materials. The spacing between nanowires as well as their diameters can be controlled through a range of methods including, but not limited to, photolithography, electron beam lithography, interference lithography, and nanosphere lithography. A combination of nanosphere lithography and catalytic etching of silicon (Peng et al., *Appl. Phys. Lett.* 90 (2007) 163123) can quickly yield periodic vertical silicon nanowire arrays with well-controlled dimensions and material properties where every nanowire has approximately the same diameter.

The nanowires may be randomly arranged or periodically arranged on the support, such as, for example, a hexagonal arrangement of nanowires. One method to form periodic nanowires is to deposit a close-packed hexagonal array of nanospheres on a precursor substrate, etch the nanospheres to make them smaller and expose portions of the substrate between the nanospheres, deposit an etching catalyst on the nanospheres and exposed precursor substrate, removing the nanospheres, and etching the substrate. This produces a hexagonal array of nanowires of approximately equal length, of the same pitch as the close-packed array of nanospheres, and of a diameter approximately the same as the reduced-size nanospheres. Other nanoparticles may also be used to form other arrangements of nanowires. For example, nanoparticles or nanospheres ranging in size from 50 nm to 1 µm in diameter can be used, as well as larger and smaller sizes. The electrode may be made of any material that is compatible with the electrical measurement to be performed. It may be any metal or other conducting material such as a transparent conducting oxide or a film of nanotubes or other nanostructures. The electrode is of any thickness and the holes may be of any diameter and spacing. There may be an electrical connection between the nanowires and the electrode. Example electrodes may be deposited from a vapor or other method and may form a continuous material. A continuous material is formed as a single article, including a layered article, rather than as a conglomeration of smaller objects such as nanoparticles or entangled filaments. Example electrode materials include, but are not limited to, a combination of titanium and gold, silver, aluminum, graphene, and a combination of chrome and gold.

The electrode contains perforations, which are open spaces forming a straight line path normal to the support and completely through the electrode. The perforations may have a diameter that is larger than the thickness of the electrode. The perforations may be randomly arranged or periodically arranged. The nanowires described above would not have exposed tips immediately under the perforations, but additional such nanowires may be present.

One example method for forming the perforations is to deposit a filler material to cover the nanowires with a filler material leaving the first ends of the nanowires exposed. This may be done at the outset or excess filler material may be removed after completely covering the nanowires. The filler material can be any material that can later be removed without removing the nanowires and electrode, including but not limited to a photoresist, an oxide, alumina, or silica. Nanoparticles are then deposited on the filler material in the locations to become the perforations. The nanoparticles may be nanospheres in a closed-packed hexagonal array with the tips of the nanowires in the spaces between nanospheres. Optionally, the size of the nanoparticles may be reduced to allow for smaller perforations. The electrode material is then deposited on top of the entire structure including the nanoparticles, the tips of the nanowires, and any exposed filler material. The nanoparticles and filler material along with the attached unwanted electrode material are then removed, leaving behind the substrate, nanowires, and perforated electrode.

Periodic perforations are formed when using close-packed nanospheres, which may be from a solution containing polystyrene (or similar) nanospheres spun on the sample. Spin-on parameters can be controlled to yield a close-packed monolayer of nanospheres on top of the nanowires. If the nanosphere diameter is equal to the nanowire-to-nanowire distance, each nanosphere will be geometrically constrained to fill in the gaps between the nanowires. The nanospheres will be prevented from resting on the tips of nanowires, which provides automatic alignment of additional nanospheres for particles to fill the void between wires. If the nanospheres are large enough, it will not be possible for more than one nanosphere to occupy the void between nanowires. However, smaller nanospheres or nanoparticles may be used to form multiple smaller perforations between adjacent nanowires.

The method may also be used to produce nonperiodic perforations if the nanowires are not periodic, if the nanoparticles are not closely packed, or other types of nanoparticles are used. By omitting the deposition of nanoparticles on top of the nanowires, non-perforated electrodes can be made on top of either ordered or non-ordered arrays of nanowires.

The structure may be used as a part of a sensor using a transduction mechanism for converting adsorbed molecules into an electrical signal. An electrical signal can be a change in voltage, current, resistance, frequency, or capacitance. A sensor typically sources (provides) a voltage or current and in turn measures the current or voltage, respectively. The measured value along with the output is used to convert to a resistance. The structure may be exposed to a sample, and then a change in an electrical property of the structure is measured. For example, the resistance between the support (or its included electrical contact) and the electrode may change in response to one or more analytes. Examples of the application of such sensors include the detection of gas or liquid-borne explosives and chemical or biological agents or toxic industrial chemicals (TICs).

Figure 1B:
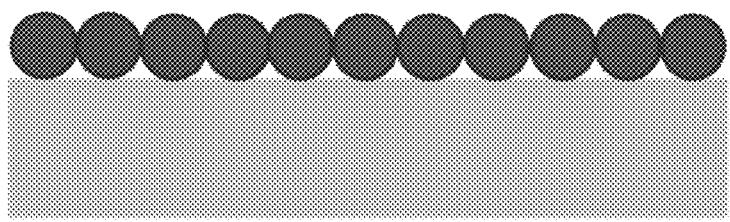
Figure 1C:
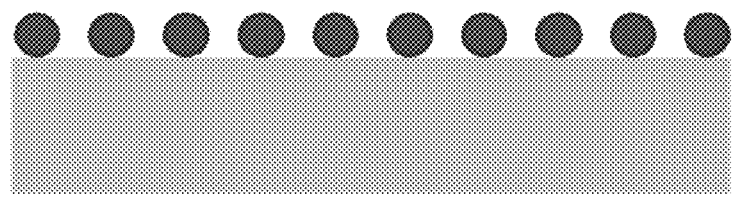
Figure 1D:
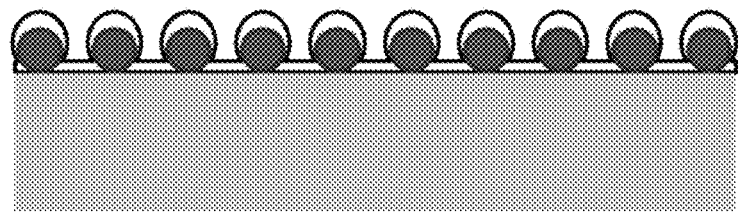
Figure 1E:
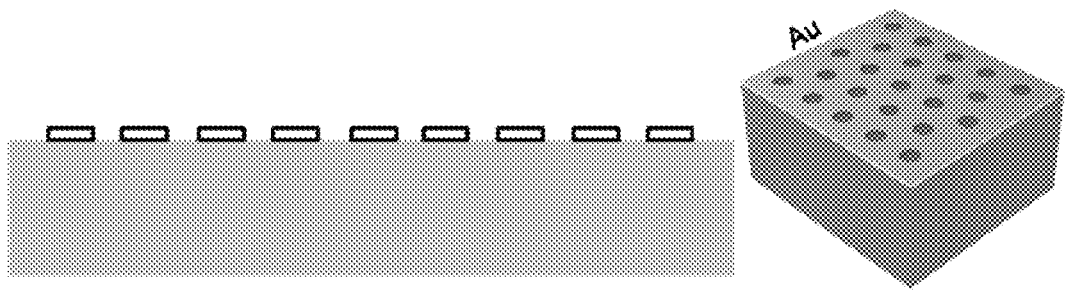

The following steps may be performed to form a structure.
Nanowire Formation
1. Start with a p-type silicon wafer with resistivity of approximately 1~10 Ω-cm.
2. Perform the following cleaning steps at room temperature (FIG. 1A):
   30 minutes in 3:1 solution of $H_2SO_4$ and 30% $H_2O_2$
   30 minutes in 5:1:1 solution of $H_2O$, $NH_4OH$, and $H_2O_2$
3. Deposit 490 nm polystyrene nanosphere solution (10% solids) on sample and spincoat to achieve close-packed monolayer (approximately 1 µL of nanosphere solution per 1 $cm^2$ of substrate) (FIG. 1B).
4. Allow sample to dry overnight.
5. Reduce nanosphere diameter to desired value using an oxygen plasma etch (FIG. 1C).
6. Deposit 25 nm of gold on top of the sample using an e-beam evaporator (FIG. 1D).
7. Remove nanospheres and unwanted metal by soaking ~5 minutes in $CHCl_3$ (FIG. 1E). Brief sonication may be necessary.

Figure 1F:
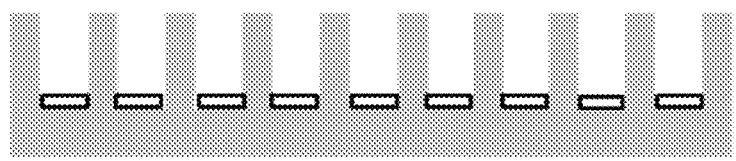
Figure 1G:
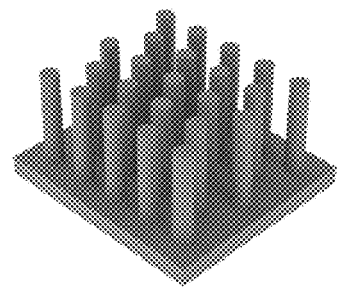

8. Etch the sample in a solution of 4.6 M HF and 0.44 M $H_2O_2$ for 20~30 minutes for nanowires around 4~8 μm in length (FIG. 1F).
9. Remove the remaining gold using a TFA gold etchant (FIG. 1G).
10. Carefully rinse and dry the sample using a critical point dryer.

Electrode Formation

Figure 1H:
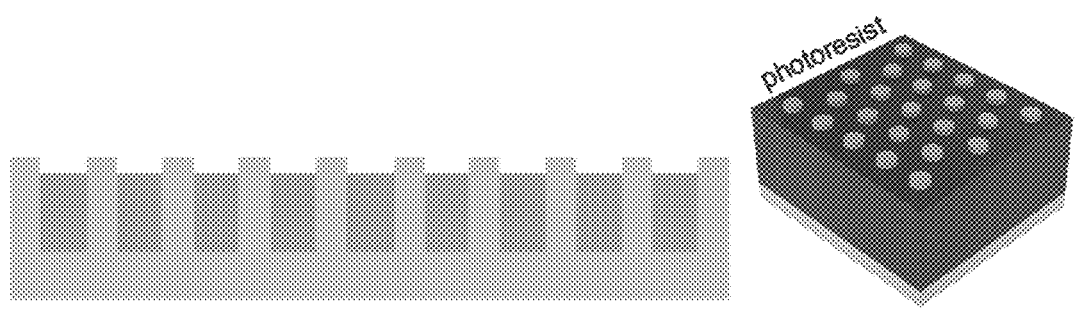
Figure 1I:
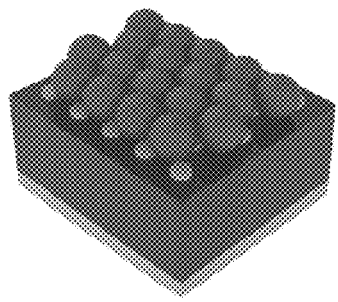
Figure 1J:
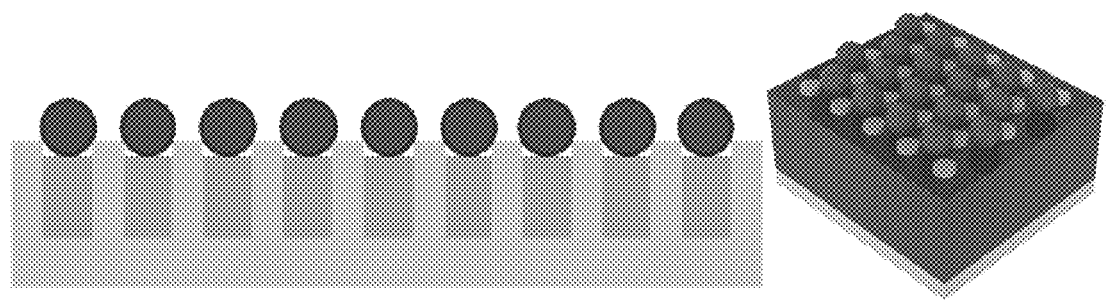
Figure 1K:
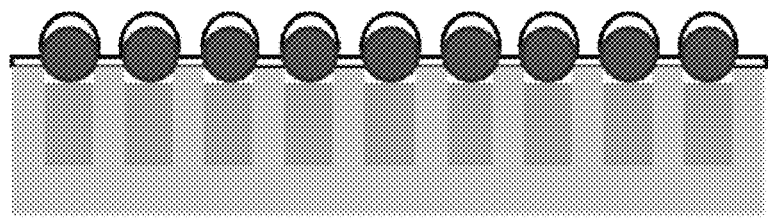
Figure 1L:
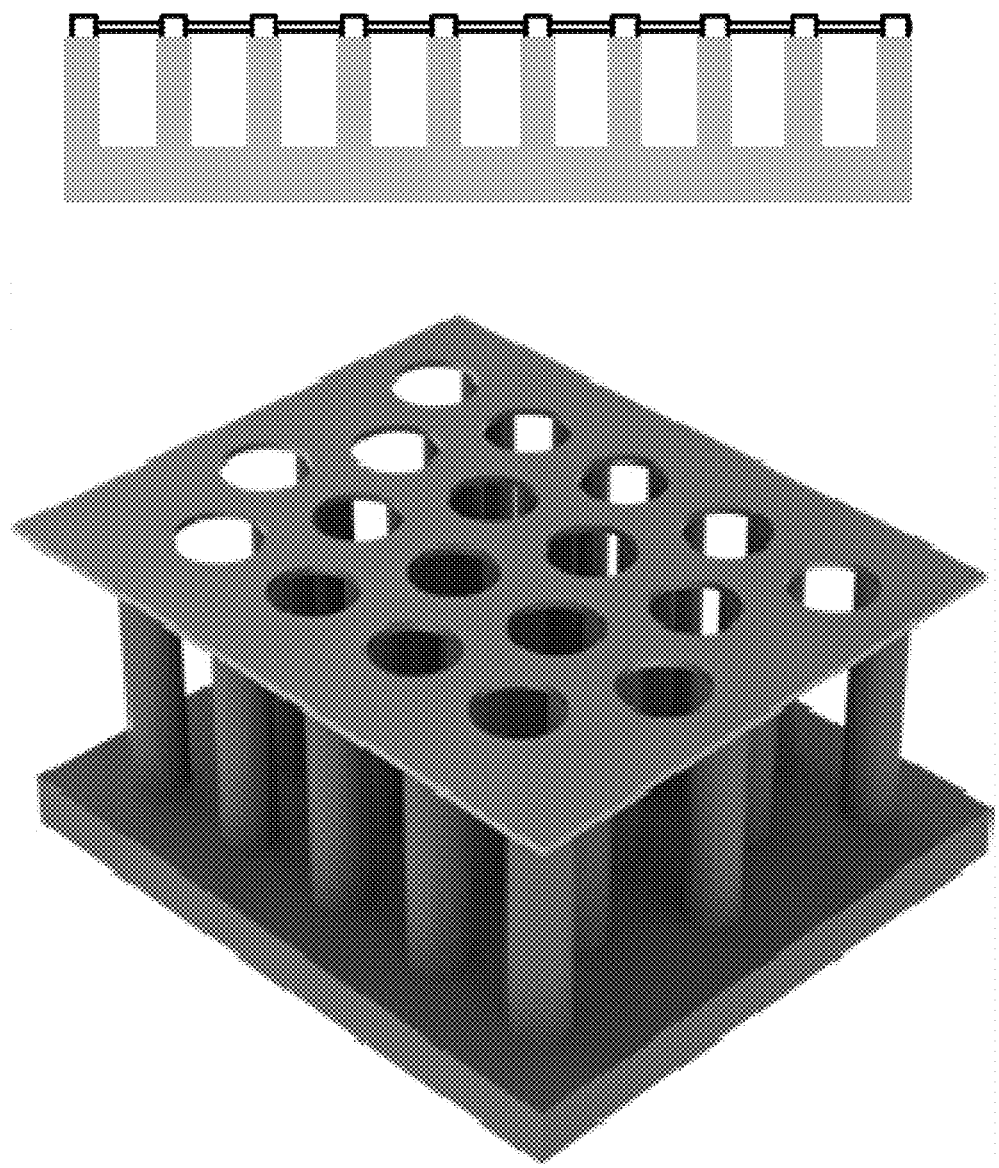

11. Deposit a thick layer of photoresist to entirely cover the nanowire array.
12. Remove the top layer of the photoresist layer using an oxygen plasma etch to reveal the nanowire tips (FIG. 1H).
13. Deposit 490 nm polystyrene nanospheres using the same process shown in step 3 (FIG. 1I).
14. Reduce nanosphere diameter to desired value using an oxygen plasma etch (FIG. 1J).
15. Deposit the electrode layer consisting of 20 nm of titanium and 100 nm of gold using an e-beam evaporator (FIG. 1K).
16. Soak the sample overnight in acetone to remove the photoresist and nanosphere layers (FIG. 1L). Brief sonication and/or soak in $CHCl_3$ may be necessary to completely remove the nanospheres.
17. Dry the sample using a critical point dryer.

In another embodiment, the nanowires are immobilized in a filler material, and then removed from the support as a unit, exposing the second ends of the nanowires. The filler material may be any material that holds the nanowires in place and can later be removed, such as a polymer or the filler materials described above. Any of the supports, substrates, nanowires, nanoparticles, electrodes, and processes described herein may be used in this embodiment.

The support may be removed from the nanowires and filler material before or after a perforated electrode is formed on the first, exposed side of the structure. In one variation, the support is removed and a perforated electrode is formed on the first side, followed by forming a second electrode on the second side. The second electrode may cover the entire second side or may be perforated by the same method as the first electrode. The second electrode may also be formed before the first. Alternatively, the first electrode is formed, then the support is removed, then the second electrode is formed. When the electrodes are formed separately, the filler material may remain present for the formation of both, or it may be removed after forming one electrode and replaced with the same or a different filler material to form the second electrode. Alternatively, the support may be removed and then both electrodes formed simultaneously.

In another embodiment, the first electrode may or may not be perforated, and the support is either a second electrode or comprises an electrical contact. Both electrodes may then be in contact with the entire array of nanowires, enabling the measurement of the electrical property through all of the nanowires.

A potential advantage of the method is the ability to form periodic perforations that are between the nanowires by an automatic process due to the self-assembly of close-packed arrays of nanospheres. No registration or alignment process is required to site the perforations. Thus the method may be scaled to large areas including entire wafers without complications due to the size of the wafer.

Potential advantages of the structure are apparent in a gas sensor type application where the geometry-enabled gas flow through the electrode and nanowire array as well as the large number of vertical nanowires connected in parallel result in gas sensing with a fast response rate and high sensitivity. To achieve maximum gas flow throughout the structure, a perforated top electrode layer can be very effective, whether the airflow is passive or actively pumped through the sensor.

Another feature of the nanosphere-enabled perforated electrode is that the properties of the holes in the top electrode, such as pitch and diameter, can be easily controlled by simply varying the size of the nanospheres deposited atop the nanowires and changing the time for which they are etched down in oxygen plasma.

The following examples are given to illustrate specific applications. These specific examples are not intended to limit the scope of the disclosure in this application.

Figure 2A:
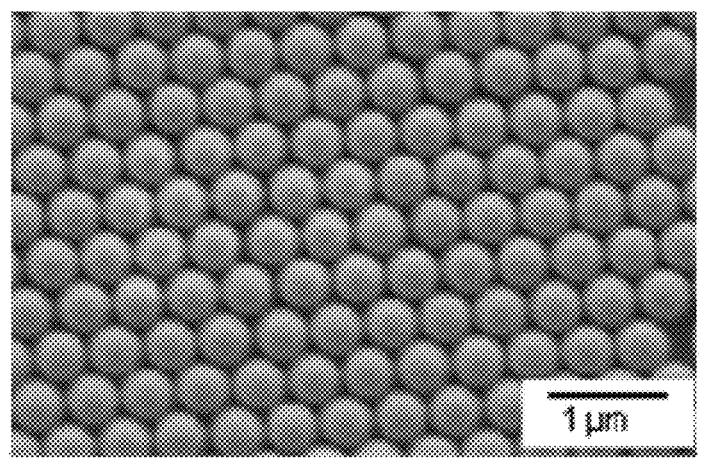
FIGS. 2A-G show scanning electron microscope (SEM) images of the structure at various stages in the fabrication process.
Figure 2B:
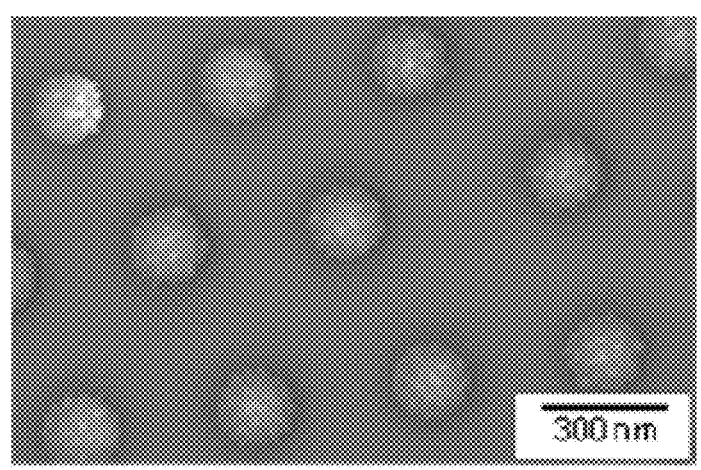
Figure 2C:
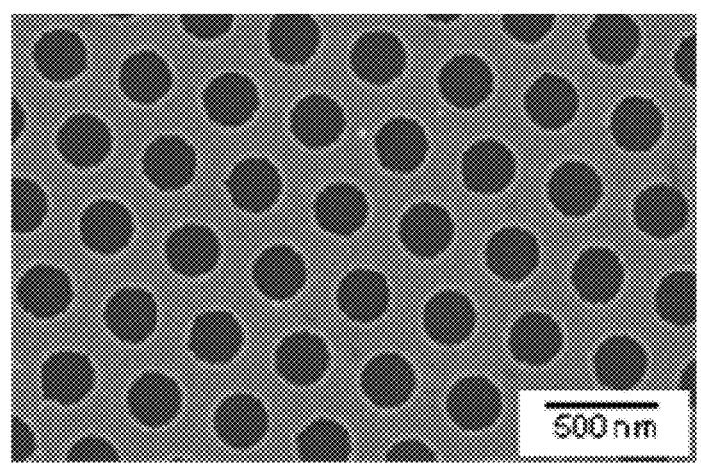
Figure 2D:
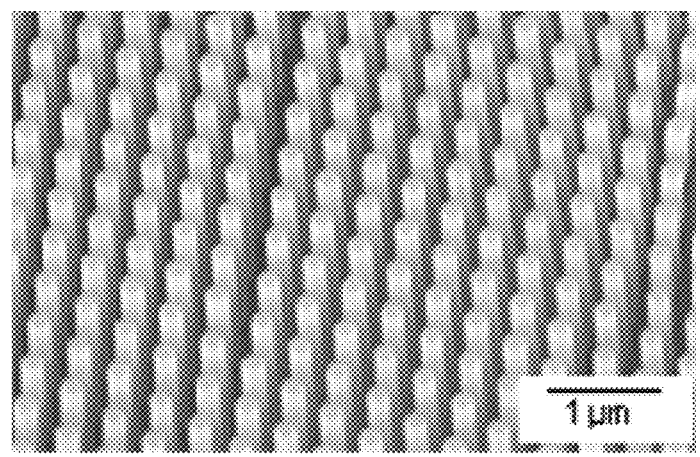
Figure 2E:
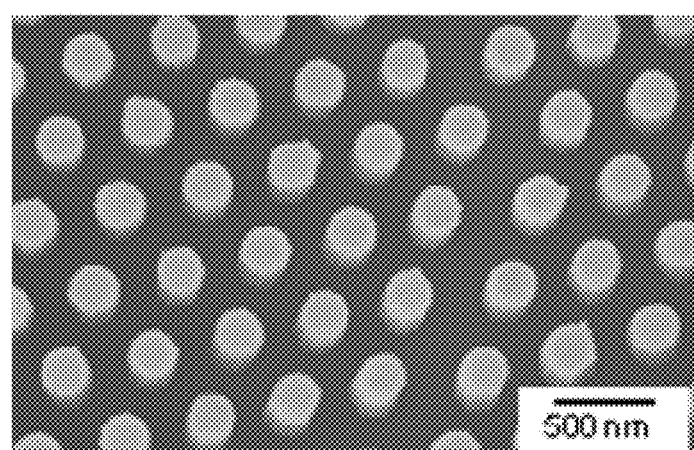
Figure 2F:
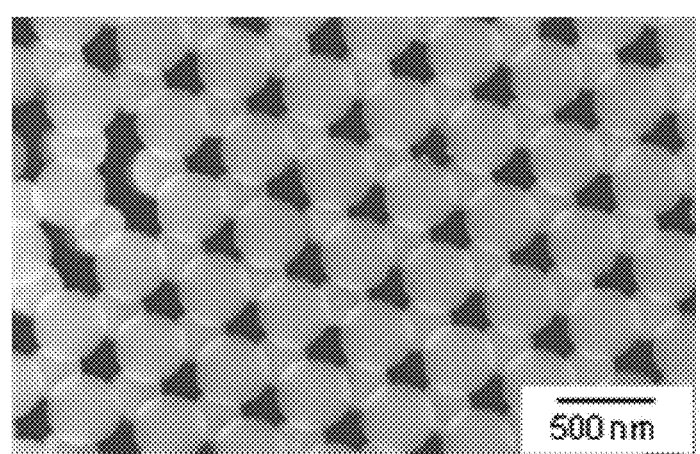
Figure 3:
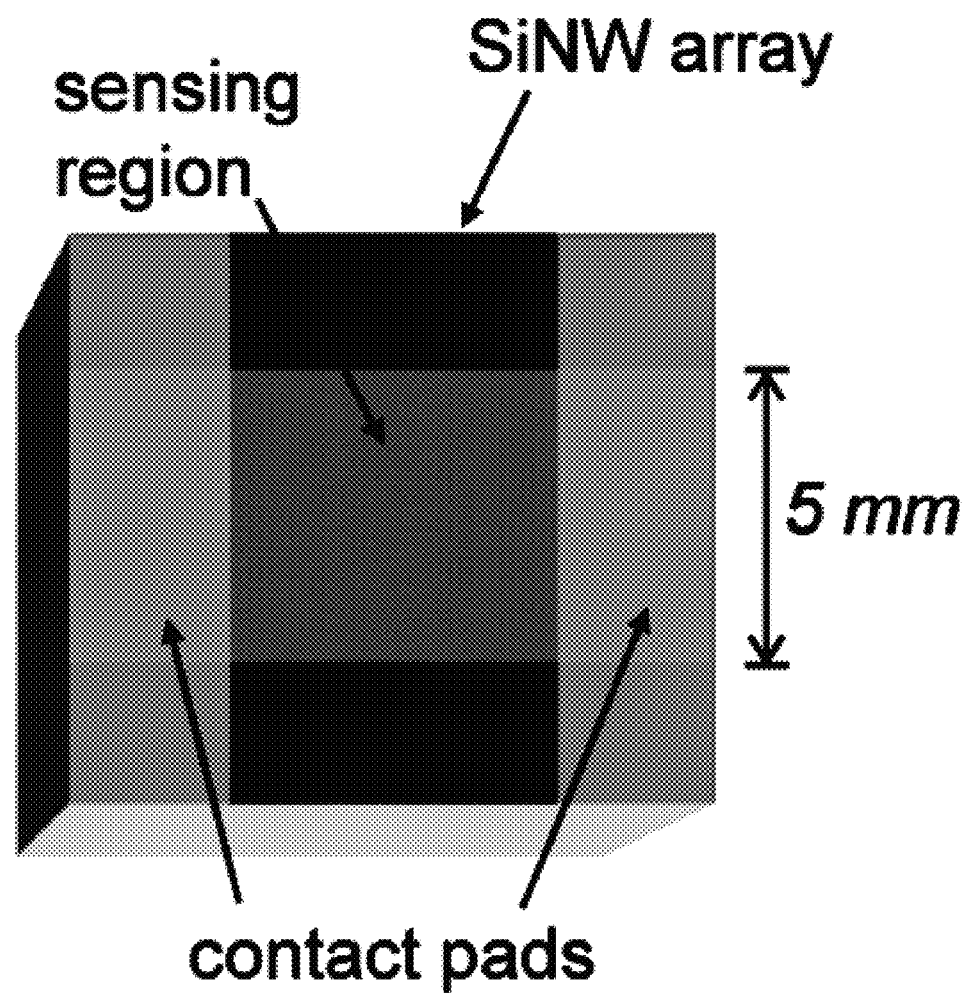
FIG. 3 shows a schematic diagram of completed device (top view).

In one study, a combination of nanosphere lithography and metal-assisted chemical etching was used to synthesize well-ordered arrays of silicon nanowires (SiNWs) (Peng et al., *Appl. Phys. Lett.*, 95 (2009) 243112). Silicon was chosen for its ease of fabrication and integration as well as the wide availability of various functionalization and surface modification techniques for increased sensitivity and selectivity. Precise control over dopant type and concentration is available in commercially obtained wafers. The process started with a 100 mm diameter B-doped p-type Si(100) wafer of resistivity ~10 Ω·cm that was cut into 1 $cm^2$ pieces and successively cleaned in a 3:1 solution of $H_2SO_4$:$H_2O_2$ (30%), 1:1:5 solution of $H_2O_2$ (30%):$NH_4OH$:$H_2O$ and deionized water. The resulting hydrophilic substrate was then spin-coated (Cheung et al., *Nanotechnology* 17 (2006) 1339-43) (FIG. 2A) with a close-packed monolayer of 490 nm polystyrene nanospheres (Bangs Laboratories, 10% w/v). The nanospheres were subsequently reduced in diameter via an oxygen plasma etch (FIG. 2B). A perforated gold template for the catalytic anisotropic etching of silicon was created by evaporating a 25 nm thick layer of gold on top of the nanosphere array and subsequently removing the nanospheres by soaking in $CHCl_3$ (FIG. 2C). The SiNWs were then formed by immersing the device in a solution of 10% HF and 0.6% $H_2O_2$, where gold selectively and anisotropically etched into the silicon substrate, leaving behind a well-ordered array of vertically standing nanowires (FIG. 2D). A photoresist layer could be patterned over parts of the template to prevent the etching of silicon in certain locations, such as the contact pad region (FIG. 3). The silicon etch rate in the HF—$H_2O_2$ solution depends on multiple factors, including solution concentration, temperature, template dimensions, etc., but was shown to be approximately 200 nm $min^{-1}$ in this case. The samples were typically etched for around 30 min to create up to ~$4\times10^8$/$cm^2$ vertical SiNWs that were 4-6 μm in length and ~200 nm in diameter, with a nanowire-to-nanowire distance of 490 nm. The initial diameter of the polystyrene nanospheres defined the SiNW array's period while the combination of this initial diameter and subsequent etching of the nanospheres in oxygen plasma defined the resulting nanowire diameter. Next, a 500 nm thick layer of $SiO_2$ was evaporated over the entire device to electrically isolate the contact pad region from the bulk of the substrate. The oxide layer was then selectively etched away to reveal the SiNW array while removing any residual oxides on the nanowire surfaces. This step also decreased the contact resistance and established ohmic contact between the nanowire tips and the electrode layer deposited later. The entire SiNW array was then covered with a thick photoresist that was subsequently etched back in oxygen plasma to reveal just the SiNW tips (FIG. 2E).

Figure 2G:
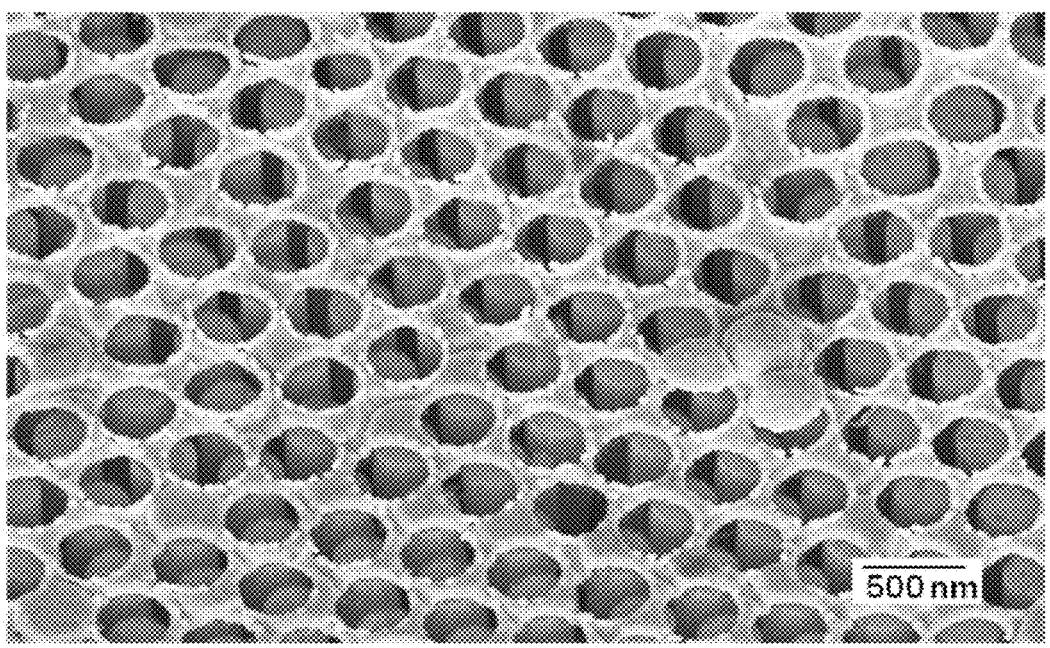

After exposing the SiNW tips, a second layer of nanospheres identical to the ones used earlier in making the etch template was deposited. Since the period of this second nanosphere layer was equal to the period of the SiNWs, the new nanospheres were physically constrained to perfectly occupy the voids in the array and form a close-packed array on top of the exposed SiNW tips. After slightly etching down the second nanosphere array in an oxygen plasma, evaporating a metal electrode layer consisting of 20 nm thick titanium and 100 nm thick gold, and finally removing the photoresist and nanospheres with acetone, a large SiNW array (5 mm×5 mm) with a PTE layer was formed as seen in FIG. 2G. Some polystyrene nanospheres are still visible in and are the result of local variations in photoresist and gold film thickness. The size and distribution of pores could be controlled by varying the nanosphere processing conditions, and the contact resistance between the nanowires and the top electrode could be reduced even further by performing a low-temperature anneal. The completed devices were mounted on pin grid array (PGA) packages using a conductive epoxy to make the bottom electrical connections. Top electrical connections were made by wirebonding to the contact pads (FIG. 3).

To evaluate the chem/biosensing capabilities of the PTE SiNW array sensors, the completed devices were exposed to varying levels of $NO_2$ or $NH_3$ in a custom-built testing chamber (Field et al., *Anal. Chem.* 83 (2011) 4724-4728). A dual manifold (an analyte line and a clean air line) was constructed out of coated stainless steel (SilcoNert Coated Stainless Steel Tubing, Restek) to minimize wall adsorption. Compressed gas cylinders of ammonia and nitrogen dioxide were connected to the analyte line of the manifold. A zero air generator (Environics) and humidity control unit (Miller-Nelson) were used to create humidified air (~40% relative humidity) for both the analyte and clean air lines of the manifold. The known concentrations of the analyte were achieved by diluting calibrated gas standards (100 ppm ammonia and 50 ppm nitrogen dioxide, Airgas) with the carrier air via a T-connector and mass flow controller. A three-way valve and actuator were used to switch between the clean and analyte lines of the manifold. The entire manifold was placed in a temperature controlled oven. A stainless steel sample chamber with a cone geometry was built for testing PGA-mounted sensors. A sample pump was used to flow air through the chamber at 100 mL/min.

Electrical connections within the sample chamber were made with a zero-insertion force (ZIF) socket and a simple printed circuit board for easy loading and unloading of sensors. A multiplexer (Keithley, 2001) and source-meter (Keithley, 2602) were connected to the circuit board of the sample chamber. The multiplexer allowed for selection of specific pins and functions of the PGA and sensor, respectively. Resistance was monitored by sourcing 100 µA of current and recording the voltage at a sample rate of 10 Hz. The sensor electronics were monitored and controlled by a LabVIEW program. The resistance recorded during exposure to clean air was averaged to obtain the initial resistance, $R_0$. The sensor response ($\Delta R/R_0$) was calculated as the difference in resistance ($R-R_0$, $\Delta R$) normalized by the initial resistance ($R_0$) for comparison and further evaluation. All data modeling and plotting were performed using the OriginPro 8.1 software package.

Without further treatment or modification of silicon, surface adsorption of electron-withdrawing (donating) species like $NO_2$ ($NH_3$) decreases (increases) the overall resistance of the p-type Si devices. A significant distinction of the this vapor delivery system is that it can mix the analytes of interest with a calibrated amount of humidified air as opposed to dry $N_2$ to simulate a real-world testing environment. Sensor testing in humidified air is a crucial step towards real-world implementation because SiNWs are highly sensitive to water vapors.

Figure 4A:
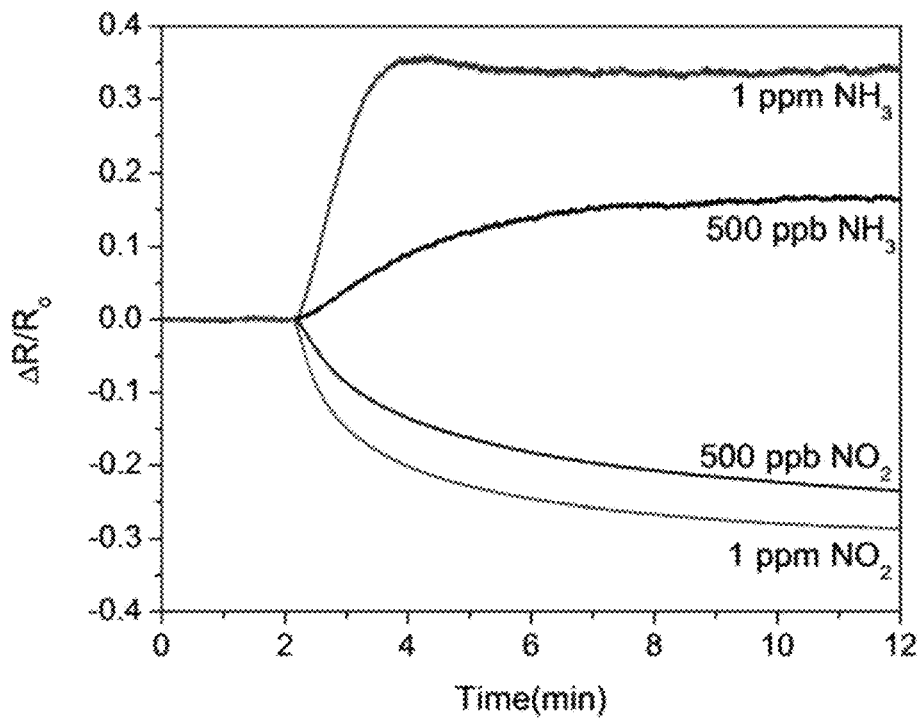
FIGS. 4A and 4B show sensor response to various concentrations of $NO_2$ and $NH_3$ following 2 min of clean air.
Figure 4B:
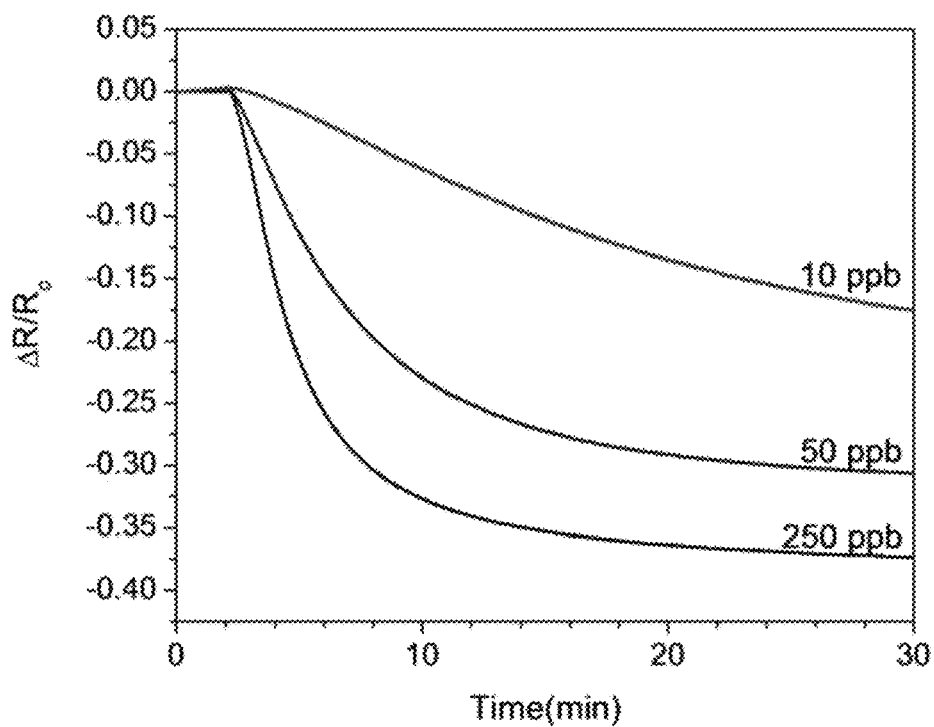

The prototype sensors were tested for response to varying concentrations of $NO_2$ or $NH_3$ at a controlled temperature of 40° C. and relative humidity of ~30%. The change in resistance was determined by holding a constant current of 10 µA while recording voltage with a voltmeter. Sensor response was plotted as the change in resistance divided by the baseline resistance ($\Delta R/R_0$), without any filtering or smoothing of the raw, real-time data. FIG. 4A shows the response of the prototype sensors to 1 ppm and 500 ppb of $NO_2$ and $NH_3$ in humidified air, respectively. As expected, total device resistance increased when exposed to $NH_3$ and decreased upon exposure to $NO_2$. The response reached saturation within a few minutes likely due to the PTE while the massively parallel nanowire configuration resulted in a very low noise profile. Humidified air adversely affects $NO_2/NH_3$ detection capabilities in metal oxide (Starke et al., *Sensors and Actuators B*, 2002, 239-45) and carbon nanotube (Zhang et al., *Nanotechnology* 20 (2009) 255501) sensors. However, water appears to improve the sensor response at very low analyte concentrations. For detection at lower concentrations, the humidity level in the testing chamber was reduced to <10% RH. Sensor response following 30 min of exposure to 250, 50, and 10 ppb of $NO_2$ is shown in FIG. 4B. For the lowest concentration level of 10 ppb, the sensor exhibited an 18% drop in resistance; 10 ppb sensitivity to $NO_2$ is among the lowest ever reported for an SiNW-based sensor and is far below various international and national requirement standards for annual $NO_2$ exposure (Belanger et al., *Am. J. Resp. Crit. Care Med.* 173 (2006) 297-303).

Figure 5A:
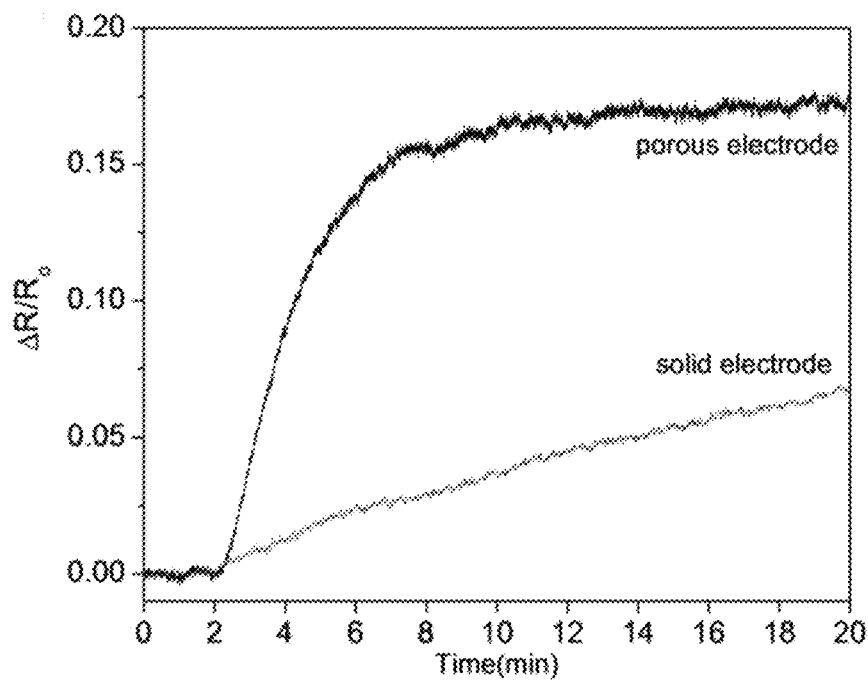
FIG. 5A shows PTE sensor and solid electrode sensor response to 500 ppb of $NH_3$ at ~30% RH.
Figure 5B:
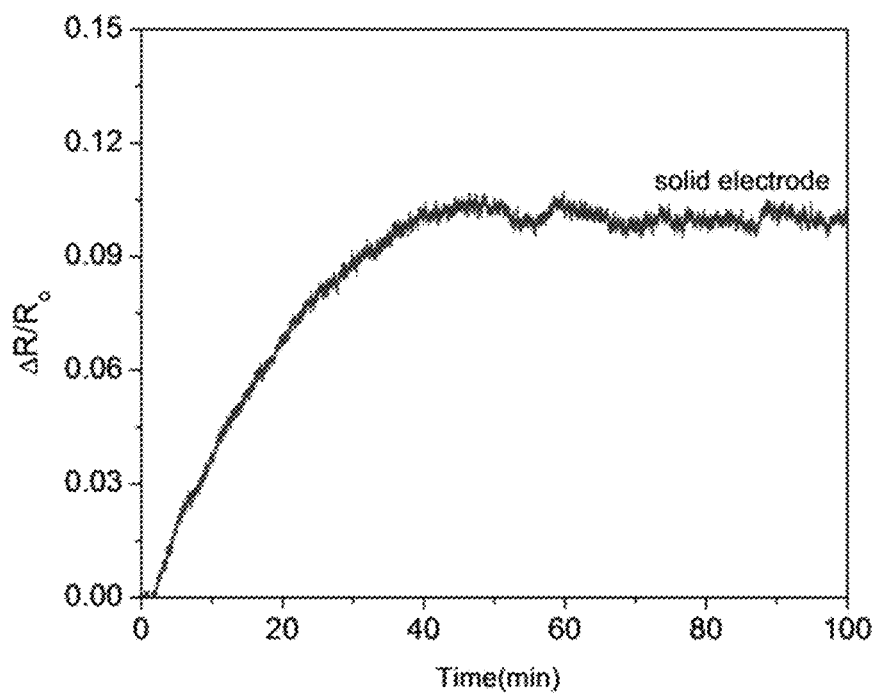
FIG. 5B shows the delayed saturation response of the solid electrode sensor.

The effect of the PTE on sensing performance was investigated by omitting the second nanosphere deposition step in the fabrication process to produce sensors with solid, non-porous electrodes. The devices with and without holes in the electrode layer were identical in all other aspects. The sensing response of both types of devices to 500 ppb of $NH_3$ is shown in FIGS. 5A-B. Both sensors reached similar saturation levels over time, but the PTE sensors, represented by the top line, reached this level in approximately 6 min. The non-porous variety, on the other hand, required almost 1 h to reach saturation. The response to $NO_2$ was also faster for the PTE sensors, albeit not as pronounced as with $NH_3$. This difference is explained by the parallel electrical configuration of the nanowires and the different resistance changes induced by the interacting molecules. $NH_3$ induces a resistance increase, so most of the nanowires must change for a large overall response by the array. In contrast, $NO_2$ decreases the individual nanowire resistance, so only a few nanowires can cause a large change in resistance for the entire array. For all detection schemes, but in particular for those resulting in increased nanowire resistance, the holes in the top electrode layer significantly improve detection response by allowing the analytes to flow directly through the electrode layer to quickly interact with all the nanowires in the array. The relative sensitivity to analyte electronegativity could be reversed by fabricating the nanowires from n-doped Si.

In another experiment, a total of six sensors from a single batch were tested. The sensors were initially exposed to clean air for 2 min, followed by exposure to either ammonia or nitrogen dioxide for 8 min. An adsorption-based sensor should follow a Langmuir adsorption model and be mass-transport limited; thus, the resistance should change asymptotically (Washburn et al., *Anal. Chem.* 81 (2009) 9499-9506; Washburn et al., *Anal. Chem.* 82 (2011) 69-72;

Eddowes et al., *Biosensors* 3 (1987) 1-15; Bunimovich et al., *J. Am. Chem. Soc.* 128 (2006) 16323-16331). The 8 min exposure time was used to determine the full rise time of the sensor response for both ammonia and nitrogen dioxide.

Figure 6:
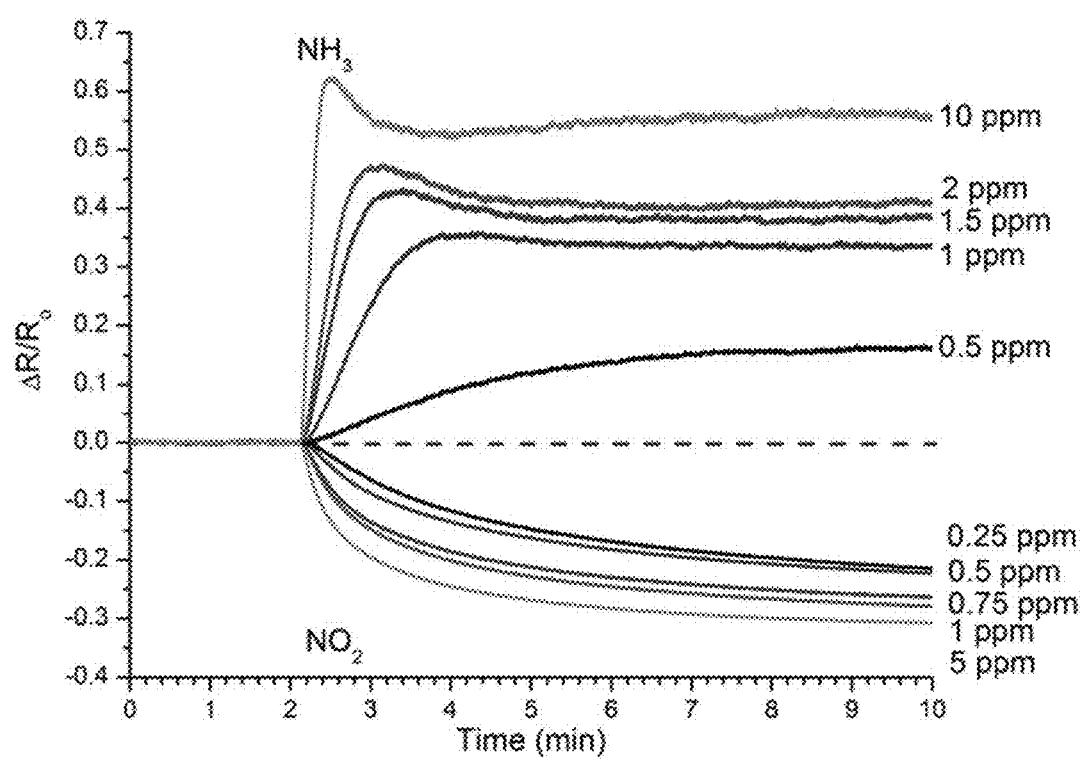
FIG. 6 shows sensor response to ammonia and nitrogen dioxide at various concentrations. The dashed line is an extension of the baseline for comparison.

The responses to ammonia or nitrogen dioxide at 40° C. at different concentrations are shown in FIG. 6. The data presented are from one representative sensor; results from additional sensors were generally consistent. The slight elevation in temperature eliminated temperature-induced fluctuations in sensor response. The concentrations of ammonia and nitrogen dioxide ranged from 250 ppb to 10 ppm. From FIG. 6, as noted and expected, the resistance increased for ammonia and decreased for nitrogen dioxide. The response saturated (leveled off) at approximately 10 min run time (8 min exposure time) for both analytes, regardless of concentration. However, the sensor needed at least 1 h of clean air exposure to partially desorb the analyte from the nanowire surfaces and return to a stable, flat baseline at 40° C. (data not shown). Because of irreversible adsorption of analytes on the nanowires, the baseline never fully recovered to its original, pre-exposure resistance but reached a new equilibrium resistance and over time the sensor lost sensitivity. The incomplete desorption of analyte from the nanowire surface during exposure limited the number of exposures and prevented replicate measurements for each concentration of ammonia or nitrogen dioxide. The recovery and lifetime can probably be improved with a higher operating temperature since adsorption/desorption is temperature dependent but is a trade-off with sensitivity and requires additional optimization. Thermal desorption of the analyte could easily be accomplished to regenerate the sensor by passing an electrical current through the wires, resulting in Joule heating and a rise in their temperature.

FIG. 6 shows the resistance change for exposure to 10 ppm ammonia, including a maximum during the initial exposure. This initial maximum is only observed at relatively high ammonia concentrations and is most pronounced at 10 ppm. No initial maximum is observed for nitrogen dioxide at any concentration, which suggests that it is analyte specific. For example, ammonia and humidified air could react to form ammonium hydroxide. Alternatively, ammonia may dissociate to $NH_2$ and H on the silicon surface, as has been observed at room temperature in ultra-high vacuum (Bozso et al., *Phys. Rev. Lett.* 57 (1986) 1185; Dillon, *J. Vac. Sci. Technol., A* 9 (1991) 2222). Dissociation would change the chemistry or restructure the silicon nanowire surface and could make the remaining surface less reactive. While the source of the initial maximum has not been definitively identified, its presence does not hinder additional analysis of the silicon nanowire-based sensor's overall response and performance.

FIG. 6 shows the rapid response as a sharp increase in resistance after exposure to ammonia following a 2 min exposure to clean air. The seconds-to-minutes saturation response of the silicon nanowire-based sensor is remarkable because the sensor is at near-room-temperature and humidified air is used as the carrier, as opposed to dry air or an inert gas. A direct comparison between sensors with porous and solid top electrodes confirmed that the porosity enables the rapid response. Modeling and simulations of the conical sample chamber (data not shown) indicate a uniform vapor front is delivered through the PTE over the entire sensor surface, thereby reducing the diffusion time for the analyte molecules to traverse the wire array.

The signal-to-noise ratio of the silicon nanowire-based sensor is markedly improved over comparable nanotube and nanowire-based sensors (Peng et al., *Appl. Phys. Lett.* 95 (2009) 243112; Lee et al., *J. Phys. Chem. B* 110 (2006) 11055-11061; Snow et al., *Chem. Soc. Rev.* 35 (2006) 790-798; Snow et al., *Nano Lett.* 5 (2005) 2414-2417; Robinson et al., *Nano Lett.* 8 (2008) 3137-3140). The signal-to-noise ratio was approximately 1000:1 for both of the analytes tested in humidified, near-room temperature air (FIG. 6). This result was obtained at a sample rate of 10 Hz and required no post-acquisition smoothing, filtering, or background subtraction. The excellent analyte response and minimal background humidity response are attributable to the PTE and the fact that every nanowire in the array is in electrical contact with both the top and bottom electrodes. Other vertically aligned nanowire-based sensors have relatively small electrodes in contact with only a fraction of the unordered nanowires, so only a small number of the nanowires act as sensing elements (Peng et al., *Appl. Phys. Lett.* 95 (2009) 243112). The PTE in the present sensor ensures that every nanowire is a sensing element in a massively parallel array that minimizes noise sources sensitive to the number of charge carriers, e.g., 1/f noise. Shot noise at the interface between the nanowires and the PTE was further minimized by removing the native oxide layer from the tips of the nanowires.

Figure 7A:
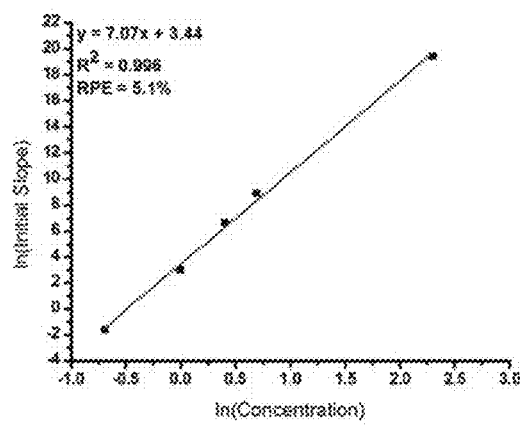
FIGS. 7A-D show the calibration curves for (FIG. 7A) ammonia and (FIG. 7B) nitrogen dioxide using an initial slope-based method and the calibration curves for (FIG. 7C) ammonia and (FIG. 7D) nitrogen dioxide using a fixed-time point method with $|\Delta R/R_0|_{saturation}$.
Figure 7B:
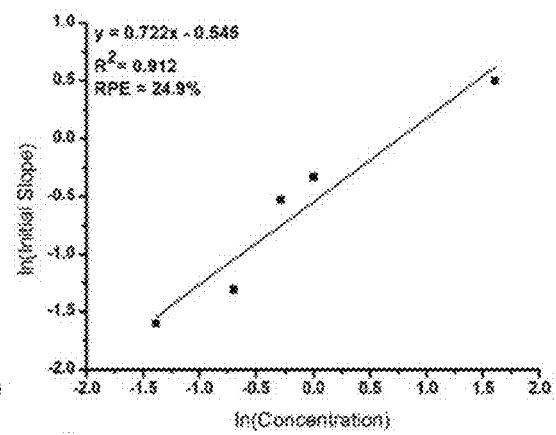

The initial slope method has been effectively used for adsorption-based sensors as a means of obtaining quantitative information, but notably in the liquid phase and for non-nanowire-based sensors (Washburn et al., *Anal. Chem.* 81 (2009) 9499-9506; Washburn et al., *Anal. Chem.* 82 (2010) 69-72; Eddowes, *Biosensors* 3 (1987) 1-15). An initial slope method allows for shorter sampling times without the need to achieve saturation and can yield a more linear calibration curve over a larger dynamic range. The sensor response at each concentration of ammonia and nitrogen dioxide in FIG. 6 was fitted to a single exponential function ($y=Ae^{-t/r}+y_0$). The slope at t=0, which is the time when the valve is switched to the analyte line, is simply, A/r. FIGS. 7A and 7B show calibration curves for ammonia and nitrogen dioxide, respectively, where the initial slope (A/r) is plotted versus concentration on a ln-ln scale.

Figure 7C:
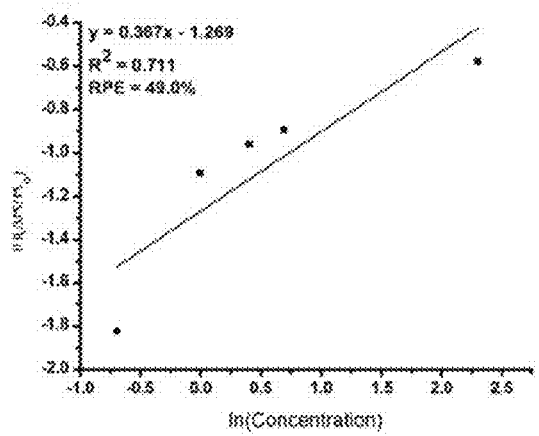
Figure 7D:
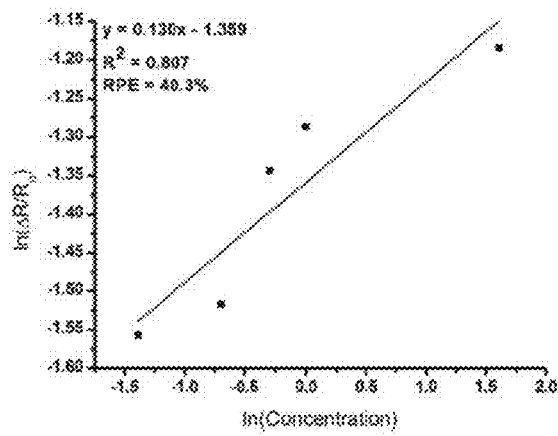

A fixed-time point method using $|\Delta R/R_0|_{saturation}$, where $|\Delta R/R_0|_{saturation}$ is the normalized response at 10 min run time, was also used to establish calibration curves for comparison (FIGS. 7C and 7D). The $R^2$ is 0.996 and 0.912 for the initial slope method and 0.711 and 0.807 for the fixed-time point method. The relative prediction error (RPE), which is the average of the error associated with each calculated concentration in the calibration curve, for ammonia and nitrogen dioxide is 5.1% and 24.9% for the initial slope method compared to 49.0% and 40.3% for the fixed time point method, respectively. Under mass-transport limited conditions, the initial slope exhibits a power law dependence that correlates better with concentration than a fixed-time point at saturation. The ammonia calibration curve is reasonable considering the curve fitting does not explicitly model the initial maximum observed at higher concentrations, but the nitrogen dioxide calibration curve can still be improved, perhaps with a better fitting model than a single exponential.

The initial slope method provides a better correlation to concentration than the fixed-time point method because it eliminates sensor saturation. This not only reduces sampling times and makes the sensor more applicable to real-world environments but improves sensor recovery and lifetime by limiting the amount of material needed for quantitation and the amount that must be desorbed to regenerate the sensor.

Obviously, many modifications and variations are possible in light of the above teachings. It is therefore to be understood that the claimed subject matter may be practiced otherwise than as specifically described. Any reference to claim elements in the singular, e.g., using the articles "a", "an", "the", or "said" is not construed as limiting the element to the singular.

What is claimed is:

1. A structure comprising:
a support;
a plurality of nanowires perpendicular to the support; and
an electrode in contact with a first end of each nanowire;
    wherein each nanowire has a second end in contact with the support; and
    wherein the electrode contains a plurality of perforations;
    wherein each perforation comprises an open space forming a straight line path normal to the support and completely through the electrode.

2. The structure of claim 1, wherein the nanowires and the perforations are periodically arranged.

3. The structure of claim 2, wherein the nanowires and the perforations are arranged as a close-packed hexagonal array.

4. The structure of claim 1, wherein there is an electrical connection between the nanowires and the electrode.

5. The structure of claim 1, wherein the support is a substrate.

6. The structure of claim 1, wherein the support is a second electrode.

7. The structure of claim 6, wherein the second electrode contains a plurality of perforations.

8. The structure of claim 1, wherein the nanowires and the support are both formed from a precursor substrate.

9. The structure of claim 1, wherein the nanowires and the support comprise silicon.

10. The structure of claim 1, wherein the electrode is formed by deposition of a vapor.

11. The structure of claim 1, wherein the electrode is a continuous material.

12. The structure of claim 1, wherein the electrode comprises titanium and gold.

13. A sensor comprising:
the structure of claim 1; and
a meter coupled to the structure to measure an electrical property of the structure.

14. A method comprising:
providing the structure of claim 1;
exposing the structure to a sample; and
detecting any change in an electrical property of the structure.

* * * * *